(12) United States Patent
Brownscombe et al.

(10) Patent No.: US 6,452,045 B1
(45) Date of Patent: Sep. 17, 2002

(54) PROCESS FOR IMPROVING YIELDS IN A DISPROPORTIONATION REACTION (HIGH YIELD HENKEL)

(75) Inventors: Thomas Fairchild Brownscombe, Houston, TX (US); James Laurel Buechele, Houston, TX (US); Donn Anthony DuBois, Houston, TX (US); Susan Secor Pfrehm, Houston, TX (US); William Larry King, Sugar Land, TX (US)

(73) Assignee: M & G USA Corporation, Akron, OH (US)

( * ) Notice: Subject to any disclaimer, the term of this patent is extended or adjusted under 35 U.S.C. 154(b) by 0 days.

(21) Appl. No.: 09/643,518

(22) Filed: Aug. 22, 2000

Related U.S. Application Data

(60) Provisional application No. 60/151,606, filed on Aug. 30, 1999, provisional application No. 60/151,577, filed on Aug. 30, 1999, provisional application No. 60/151,607, filed on Aug. 30, 1999, provisional application No. 60/151,498, filed on Aug. 30, 1999, provisional application No. 60/151,602, filed on Aug. 30, 1999, provisional application No. 60/151,603, filed on Aug. 30, 1999, provisional application No. 60/151,529, filed on Aug. 30, 1999, provisional application No. 60/151,489, filed on Aug. 30, 1999, provisional application No. 60/151,604, filed on Aug. 30, 1999, provisional application No. 60/151,589, filed on Aug. 30, 1999, provisional application No. 60/151,497, filed on Aug. 30, 1999, provisional application No. 60/151,590, filed on Aug. 30, 1999, and provisional application No. 60/151,578, filed on Aug. 30, 1999.

(51) Int. Cl.$^7$ ................. C07C 51/347; C07C 63/33; C07C 55/28
(52) U.S. Cl. ................. 562/481; 562/481; 562/488; 562/490; 562/492
(58) Field of Search ................. 562/481, 488, 562/490, 492

(56) References Cited

U.S. PATENT DOCUMENTS 3,873,608 A * 3/1975 Laurence et al.

OTHER PUBLICATIONS

Porter et al, Analytical Calorimetry, 1974, vol. 3, p. 538, Plenum Press, New York.*

* cited by examiner

*Primary Examiner*—Sreeni Padmanabhan
*Assistant Examiner*—Farhad Forohar
(74) *Attorney, Agent, or Firm*—Renner, Kenner, Greive, Bobak, Taylor & Weber

(57) ABSTRACT

Disclosed is a process for disproportionation of potassium naphthoate to the dipotassium salt of 2,6-NDA which gives reproducible improved yields of up to 40% which comprises:

a) reacting naphthoic acid in the presence of excess base to produce a disproportionation feed comprising a finely dispersed disordered salt mixture of excess base salts and naphthoic acid salts, wherein the feed is prepared by the steps of:
   (1) Reacting naphthoic acid in the presence of excess base selected from the group consisting of carbonates and bicarbonates to form a salt;
   (2) Drying said salt mixture by a method which forms a highly mixed disordered salt mixture characterized by a differential scanning calorimeter(DSC) signature characterized by low melting peaks not previously observed in the salt; and b) Disproportionating said solid salts in the presence of a disproportionation catalyst to form the dipotassium salts of 2,6-NDA.

28 Claims, No Drawings

PROCESS FOR IMPROVING YIELDS IN A DISPROPORTIONATION REACTION (HIGH YIELD HENKEL)

This application claims the benefit of U.S. Provisional Application No. 60/151,606, filed Aug. 30, 1999, the entire disclosure of which is hereby incorporated by reference.

CROSS REFERENCE

This application is related to U.S. application Ser. No. 60/151,577 filed Aug. 30, 1999, Ser. No. 60/151,607 filed Aug. 30, 1999, Ser. No. 60/151,498 filed Aug. 30, 1999, Ser. No. 60/151,602 filed Aug. 30, 1999, Ser. No. 60/151,603 filed Aug. 30, 1999, Ser. No. 60/151,529 filed Aug. 30, 1999, Ser. No. 60/151,489 filed Aug. 30, 1999, Ser. No. 60/151,604 filed Aug. 30, 1999, Ser. No. 60/151,589 filed Aug. 30, 1999, Ser. No. 60/151,497 filed Aug. 30, 1999, Ser. No. 60/151,590 filed Aug. 30, 1999, and Ser. No. 60/151,578 filed Aug. 30, 1999.

FIELD OF THE INVENTION

This invention relates to disproportionation/isomerization reactions, such as the Henkel reaction. More particularly, this invention relates to the disproportionation of the salt of a monocarboxylic acid, such as potassium naphthoate, to form the salt of a dicarboxylic acid, such as the salt of isomers of naphthalene dicarboxylic acid. Still more particularly, this invention relates to a combination of modifications of the elements of a disproportionation reaction that provides improvements in product yield of as much as 40%.

BACKGROUND OF THE INVENTION

Aromatic dicarboxylic acids are highly useful organic compounds. They are often used as monomers for the preparation of polymeric materials. 2,6-naphthalene dicarboxylic acid (2,6-NDA) is a particularly useful aromatic carboxylic acid, because it can be reacted with ethylene glycol to prepare poly(ethylene-2,6-naphthalate), PEN. Fibers and films manufactured from PEN display improved strength and superior thermal properties compared with other polyester materials such as polyethylene terephthalate. High strength fibers made from PEN can be used to make tire cords, and films made from PEN are advantageously used to manufacture magnetic recording tape and components for electronic applications.

It is known in the art to prepare aromatic dicarboxylic acids such as 2,6-NDA by primarily two methods. One is the liquid phase, metal catalyzed oxidation of an alkyl or acyl substituted aromatic compound. This method is described, for example, in U.S. Pat. Nos. 2,833,816; 3,856,855; 3,870,754; 4,933,491; and 4,950,786.

Alternatively, naphthalene monocarboxylic acid and naphthalene dicarboxylic acids other than 2,6-naphthalene dicarboxylic acid can be converted to 2,6-NDA, using a disproportionation reaction in the case of the monocarboxylic acids, or a rearrangement reaction in the case of other naphthalene dicarboxylic acids. Henkel and Cie first patented a reaction of naphthoic acid salts to 2,6 NDA in the late 1950s. (See U.S. Pat. No. 2,823,231 and U.S. Pat. No. 2,849,482). In these references, the product yield of the disproportionation reaction is about 65% at best. Of course it would be desirable to improve on these yields.

Currently in the art 2,6-NDA for commercial use is prepared by oxidation, even though that route is plagued with difficulties. The most common process for making 2,6 NDA starts with relatively expensive o-xylene and butadiene feedstocks, as discussed, for example, in U.S. Pat. No. 5,510,563 and U.S. Pat. No. 5,329,058 and incurs substantial yield losses of these starting materials. Following the synthesis and purification of 2,6 dimethylnaphthalene (2,6 DMN), 2,6 DMN is oxidized to produce crude NDA product which forms as a solid with impurities trapped within. In order to remove these impurities to a sufficiently low level acceptable for polymerization, the 2,6 NDA product must be purified via multiple steps. These steps typically involve esterification, so that the end product is 2,6-naphthalene dicarboxylate, an ester, rather than the preferred 2,6 napthalene dicarboxylic acid. Esterification to naphthalene dicarboxylate (NDC) is necessary to eliminate the impurities, as discussed in U.S. Pat. No. 5,254,719 and 4,886,901.

Various improvements in a route to NDA based on disproportionation/rearrangement have been claimed in the art. In this work Henkel preparations which claimed to have improved yields depended on catalysts containing halogen-containing corrosive salts or other toxic and irritating materials. Other research that used zinc as a catalyst reported the making of zinc salts of the aromatic acids, a process involving added capital and difficulty in recycling the zinc. Yields of these processes were, even so, low due to failure to observe the effect of the critical components of the reaction and the effect of their ranges on the result of the reaction.

U.S. Pat. No. 2,919,273 claims improvements in yield in the thermal rearrangement of salts of cyclic carboxylic acids using as the catalyst salts of catalytically-active bivalent metals, wherein said metals are present in the form of compounds of the general formula selected from the group consisting of $Alk_2(MeX_2Y_2)$ and $Alk(MeX_2)$, where Alk is an alkali metal cation, Me is a bivalent catalytically active metal selected from the group consisting of cadmium, zinc and lead, and X is a halogen ion and Y is an ion selected from the group consisting of halogen and carbonate ions. This reference does not specifically address or have examples of disproportionation of potassium naphthoate.

The object of U.S. Pat. No. 3,641,130 is to obtain greater efficiency in a disproportionation reaction and claims an advantage carrying out said reaction in the presence of at least one adjuvant compound of the formula R—X—M, wherein R is an alkyl, cycloalkyl, aryl radical, or combination thereof having from 1 to 15 carbon atoms therein, X is oxygen or sulfur, and M is hydrogen or an alkali metal.

U.S. Pat. No. 3,751,456 claims an improvement in a disproportionation reaction using as a catalyst a mixture of cadmium iodide and sodium iodide.

U.S. Pat. No. 3,875,218 claims advantages using as a catalyst a metal salt of an aromatic carboxylic acid, said metal being selected from the group consisting of zinc, cadmium, mercury, lead, and iron. The examples demonstrate the use of zinc benzoate.

U.S. Pat. No. 4,820,868 claims an improvement in a process for the preparation of a naphthalene 2,6-dicarboxylic acid dialkali metal salt comprising using naphthalene as a reaction medium, wherein the amount of naphthalene is 0.5 to 10 times the amount of the starting material by weight.

There is still a need in the art for greater conversion and yield in the production of 2,6-NDA, the preferred monomer for the production of polyethylenenaphthalate (PEN).

An object of the present invention is to improve rates of conversion to 2,6- naphthalene dicarboxylic acid (2,6-NDA). Another object is to increase the total yield of 2,6-NDA.

SUMMARY

The present invention provides a method for increasing the disproportionation yields (Henkel II) of the dipotassium salts of 2,6-NDA from ca. 70% to as much as 95–100%, or more, resulting in a far more economical process. (Yields in excess of 100% basis the formal disproportionation reaction are possible provided some of the naphthoate salt starting material is carboxylated instead of disproportionated).

In accordance with the foregoing the present invention provides a process for disproportionation of potassium naphthoate to the dipotassium salt isomers of 2,6-NDA with reproducible improved yields which comprises reacting naphthoic acid in the presence of excess base to produce a feed comprising a finely dispersed disordered salt mixture of excess base salts and naphthoic acid salts, wherein the feed is prepared by the steps of:
  a) Reacting naphthoic acid in the presence of at least 0.001 to 0.30 moles of excess base (excess beyond the amount necessary to form naphthoate salt of 1:1 acid to cation ratio) selected from the group consisting of carbonates and bicarbonate to form a solid salt;
  b) Drying said salt mixture by a method which forms a highly mixed disordered salt mixture characterized by:
    (1) A differential scanning calorimeter(DSC) signature characterized by low melting peaks not previously observed in potassium naphthoate salt; and/or
    (2) A characteristic Xray diffraction pattern.
  c) Disproportionating said solid salts in the presence of a disproportionation catalyst to form the dipotassium salts of 2,6-NDA.

DETAILED DESCRIPTION OF THE INVENTION

When preparing feed salts for the Henkel disproportionation reaction in literature of the prior art, care is usually taken to prepare organic salts of precise stoichiometry. Raecke, (See U.S. Pat. No. 2,823,231) for example, back-titrated potassium acid salts with aqueous HCl to produce a solution of pH 6–7, resulting in a ratio of about 0.96(or less) to 1.00 potassium: aromatic acid. Using this sort of procedure yields are typically 60–70% of theoretical. In the present invention we have discovered process conditions that provide a reproducible yield of as high as 98% or more for naphthoic acid salt disproportionation to 2,6-NDA as opposed to published yields of about 65–75%.

Normally when employing a disproportionation reaction such as the Henkel, a significant yield loss occurs during the reaction. This loss, even in the best of circumstances, is usually 3% or more of the weight of the naphthalene dicarboxylic acids (NDAs) theoretically expected to be produced. This loss arises from a mixture of causes, such as coupling of aromatic radicals to form binaphthyls and higher condensed species, decarboxylation of naphthoic acids to naphthalene, and other undesired reactions. In the absence of charging other carboxylic acid salts (e.g. tricarboxylic benzene acids, or potassium formates and the like) there is no precedent for obtaining a yield of NDA which exceeds the theoretical yield given by the equation for the Henkel II reaction:

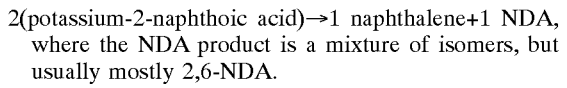

2(potassium-2-naphthoic acid)→1 naphthalene+1 NDA, where the NDA product is a mixture of isomers, but usually mostly 2,6-NDA.

In the present invention we have found the process elements that are the most critical in obtaining reproducible high yields. The inventive process consists of using an excess base, particularly an excess of the carbonate and bicarbonate salts formed by the $CO_2$ precipitation of 2,6-NDA in the acid form. The process also involves preparation of a finely dispersed mixture of the excess base salts with the naphthoic acid salts which are characterized by observable low melting peaks in differential scanning calorimeter (DSC) scans of the feed salts. Further, the reaction may be accelerated by the addition of small amounts of larger alkali cation salts (e.g. Cs) which also seem to depress the melting point and improve the mixing of the carbonic and naphthoic salts. The key elements for producing higher yields of 2,6-NDA are:

1) Preparation of a disproportionation feed of finely dispersed salt materials containing a particular XRD diffraction pattern and differential scanning calorimeter (DSC) signature characterized by low melting peaks not usually observable in the naphthoic acid salt, prepared using 0.001 to 0.30 moles of excess base, preferably 0.03 to 0.30 moles of excess base, for each mole of naphthoic acid and preferably containing an effective amount of disproportionation catalyst, preferably a Group IIb metal salt, most preferably Zinc oxy salts; and 2) Strict regulation of the amount of water present, to ca. 1000 ppm, obtained by predrying the salt of naphthoic acid; and In addition, the following elements of the process appear to contribute to the desired high yields:

3) The use of carbonate or bicarbonate, or mixtures thereof, as the base to form the potassium salts of naphthoic acid;

4) The use of zinc compound as the disproportionation catalyst;

5) Use of at least 100 psig of $CO_2$ as a gas cap, preferably less than 500 psig, and most preferably about 250 psig;

6) Use of heat transfer media to provide a uniform vessel temperature for the reacting salt particles regulated to a constancy of </=ca. 10° C.; and 7) Optional use of liquid diluents such as naphthalene.

The starting material used in the present invention is a salt of an aromatic carboxylic acid, such as an alkali metal salt of benzoic acid, but particularly an alkali metal salt of naphthoic acid, a dialkali metal salt of naphthalene dicarboxylic acid, or a mixture thereof. As the alkali metal salt of naphthoic acid, there may be used a 1-isomer, a 2-isomer, and a mixture thereof. As the dialkali metal salt of naphthalene dicarboxylic acid, there may be used a 1,2-isomer, a 1,3-isomer, a 1,4-isomer, a 1,5-isomer, a 1,6-isomer, a 1,7-isomer, a 1,8-isomer, a 2,3-isomer, a 2,6-isomer, a 2,7-isomer, or a mixture thereof. The feed used to exemplify the invention was an alkali salt of naphthoic acid. The naphthoic acid was a combination of the 1-isomer and 2-isomer.

Suitable bases include alkali metal carbonates. The alkali metal can be selected from the group consisting of lithium, sodium, potassium, rubidium, and cesium, but is preferably potassium. Bases which can be used to provide the excess include, but are not limited to, $K_2CO_3$, $KHCO_3$, $Rb_2CO_3$, $RbHCO_3$, $Cs_2CO_3$, $CsHCO_3$, and other strongly basic carbonates or bicarbonates. We have found it advantageous to use potassium carbonate or potassium bicarbonate. Potassium hydroxide will work, but for the purposes of the present invention, carbonates and bicarbonates are preferred.

Suitable temperatures for a disproportionation reaction are generally in the range of from about 340° C. to 500°, and usually in the range of from about 400° C. to 480°. The temperature range is dictated by specific salts and conditions and the selected temperature should be as uniform as possible. The preferred temperature in the present invention is from about 440° C. to 460° C. In the present invention, the use of heat transfer media assists in providing a uniform vessel temperature for the reacting salt particles with the objective of keeping the temperature within 10° C. of the desired temperature of the disproportionation reactor.

Reacting naphthoic acid with excess base is a critical element of the present invention. An excess of base to naphthoic acid in the range of 1.01–2.0:1 is within the inventive concept, however greater than 2:1 is too high, because the organic part of the mixture will be too dilute. The benefits of the excess base are accomplished within the range of 1.03–1.8:1, preferably 1.1–1.6:1, moles potassium to moles of acid; and it is believed that, generally, about 1.15 to 1.3:1 moles of base to naphthoic acid will ensure reproducible improved yields. The optimum level of "overbasing" is between 0.001 and 0.3 moles of excess base per mole of naphthoic acid, although this is probably a function of the exact formulation and conditions used. Good results were obtained using 0.03 to 0.20 moles of excess base per mole of acid. It will be obvious to those skilled in the art that subsequent separation of the naphthalene dicarboxylic acid product will be more difficult, the more base is used.

The catalyst providing the best results in conjunction with the combination of conditions used for disproportionation in the present process is preferably a zinc compound. A number of zinc compounds would be suitable, including zinc halides such as zinc fluoride, zinc chloride, zinc bromide, and zinc iodide; zinc carboxylates such as zinc naphthoate and zinc naphthalene-dicarboxylate; zinc oxide, zinc carbonate; zinc sulfate and mixtures thereof. The zinc salts, preferred for cost and low toxicity, may be used as the oxide, carbonate, or other inorganic salt of the naphthoic acid feed, conveniently formed by reaction of the naphthoic acid with zinc oxide under elevated temperature. However, in the preferred embodiment the catalyst employed was ZnO.

A key part of the present invention is the preparation of disproportionation feed comprising a finely dispersed mixture of the excess base salts with the naphthoic acid salts. The excess base and potassium naphthoate can be mixed in water in almost any concentration, however greater than about 5% solids is preferred due to the lesser requirement for heating to remove the water and form the solid feed. The zinc catalyst as zinc oxide can be suspended as a solid in the mixture or it can be reacted with naphthoic acid to make zinc naphthoate, which can also be mixed in with the base and potassium naphthoate. It is noted, however, that the use of zinc oxide would dictate one set of drying conditions, while the use of zinc naphthoate would indicate other drying conditions, as would be apparent to one skilled in the art.

These salt mixtures, prepared as described, result in characteristic xray diffraction patterns which seem to be indicative of feeds which will provide higher yields. The powder xray diffraction patterns of the initial gently dried or air exposed feed salt mixture which will comprise the preferred feed is characterized by one or more of the following "two theta" peaks (among others): 14.0, 28.5, 38.2, 13.6, 27.3, 32.0, and 36.7 degrees two theta. Not all the peaks need be in all samples, but in general feeds which have these peaks (as well as others) will give good yields. These peaks correspond to lattice spacings of 6.32, 3.13, 2.35, 6.52, 3.26, 2.80, and 2.45 Angstroms in Bragg d-spacing.

We have found a critical element in the process is maintaining the amount of water present in the disproportionation reactor to less than or about 1000 ppm. This is accomplished by drying the potassium naphthoate salt before disproportionation, "predrying" as will be discussed below. Although too much water can present problems, it has been observed in the present invention that a small amount of water seems to actually be beneficial. It is speculated the beneficial effects are due to the effect of the water of introducing increased mobility into the salts, specifically allowing the salt complexes more rotational freedom and also by stabilizing the charged species formed as intermediates. It is also possible a small amount of water stabilizes the original finely divided mixed crystalline low melting materials that make the best feeds. However, a significant amount of water, say, for example in excess of ca. 700–1000 ppm, interferes with the reaction by beginning to favor the decomposition of the salts (decarboxylation). A significant amount of water, 0.2% or more, becomes damaging by promoting yield loss.

The goal of the drying step is to achieve a product salt that is a highly disordered salt mixture that is intimately mixed and to reduce any water present to less than 1000 ppm. Drying can be accomplished by heating the solids at about 150–200° C., preferably about 175° C. for about 1–3 hours, preferably about 2 hours under 0.8 torr mm Hg pressure. The Hg pressure in some instances might be higher, say as high as 2 torr, or higher. As mentioned above, drying can also be achieved by dripping the naphthoic acid potassium salt and carbonate aqueous mixture into hot oil. The mixture can also be spray dried, dried in a rotary evaporator or tumbler, or dried by some other method which quickly flashes water and forms a product with preferably small crystals.

It is desirable that the material be as intimately mixed as possible; the closer to molecular mixing, the better. The preferred salt feeds are also characterized by at least one or more low temperature DSC melt peaks not associated with pure potassium naphthoate or carbonate. There will be observable peaks in the range of about 2600 to 350° or so, well below the expected peaks around 400° C.

Thermogravimetric Analysis (TGA) of preferred feeds will reveal a relatively low onset temperature of non-drying weight loss as described in Example 8 and in copending U.S. Patent Application Ser. No. 60/151,604, incorporated herein by reference in the entirety.

A convenient way of forming the preferred disordered salt mixture is to charge a mixture of the organic naphthoic acid potassium (or mixed alkali) salt in water with dissolved inorganic (carbonate, bicarbonate) salts and suspended zinc oxide into a vessel of hot oil, preferably naphthalene or another stable hydrocarbon consistent with the process. Hot naphthalene, which has a boiling point 100–200° C. above the salts, flashes water, and produces a porous and finely dispersed product. By this means the solution is rapidly converted to a porous solid of comparatively fine crystallite size and intimately mixed organic and inorganic salts. In order to analyze precisely for the amount of products produced, three repeated extractions of the salt phase with KOH in $D_2O$ and a suitable protonic internal standard for nmr (TSP, trimethyl sillyl sodium propionate) were made to analyze for the acids by quantitative nuclear magnetic resonance, and the hydrocarbon (naphthalene) portion of the product was digested in d6 DMSO (deuterio dimethyl sulfoxide) with trioxane as the internal protonic standard. By using test synthetic salt mixtures of K2-2,3 NDA, K2-2,6 NDA, K-2-NA, and naphthalene, it was shown that the error in the analysis by this method was less than 1% mole of the contained species analyzed.

A eutectic mixture can optionally be employed in the present invention. A eutectic mixture provides the lowest melting point of a mixture of two or more alkali metals that is obtainable by varying the percentage of the components. Eutectic mixtures have a definite minimum melting point compared with other combinations of the same metals. For example, though the melting point of $Li_2CO_3$ is 622° C., in a eutectic mixture of alkali carbonates the melting point can be 400° C. What is required, where a eutectic mixture is employed, is the right mixture of alkali metal carbonates where the melting point is less than about 400° C. Generally the ratio of alkali metal carbonates in the eutectic mixture is about 1:1:1, but it can vary. One eutectic mixture used as a solvent was $K_2CO_3$, $Rb_2CO_3$, $CS_2CO_3$, and optionally $Na_2CO_3$.

In most disproportionation reactions one can observe in the art, suitable $CO_2$ pressures are from about 200 to 10,000 psig. A more preferred range is generally from about 350 to 1100 psig. We have discovered that higher pressures will work, but there may be disadvantages with respect to costs and other factors. In combination with the other specified conditions of this process, a lower pressure worked very satisfactorily in contributing to better yields. A suitable $CO_2$ pressure should be above 100 psig and good results were achieved using no higher than 500 psig. In the examples the preferred range is about 225–275 psig.

The reaction medium for the disproportionation reaction of the present invention is optionally and suitably naphthalene, but it can be any compound with sufficient thermal stability. It is not restricted to aromatic compounds, however aromatic compounds are suitable. Examples of suitable solvents include a single compound or mixture of compounds selected from a variety of aprotic polycyclic aromatic compounds, such as, for example, naphthalene, methylnaphthalene, dimethylnaphthalene, diphenyl ether, dinaphthyl ether, terphenyl, anthracene, phenanethrene, and mixtures thereof.

In the present invention a slurry containing the solid particulate salts and ZnO catalyst is fed to the disproportionation reactor at a temperature of about 450° C. and about 250 psi, $CO_2$ headspace, where KNA disproportionates to the dipotasium salt of 2,6 NDA and naphthalene. The reaction time can be up to three hours. The optimum residence time is about 1 to 1½ hours.

The following examples will serve to illustrate specific embodiments of the invention disclosed herein. These examples are intended only as a means of illustration and should not be construed as limiting the scope of the invention in any way. Those skilled in the art will recognize many variations that may be made without departing from the spirit of the disclosed invention.

EXAMPLE 1

Example 1 describes the method of preparing the feed salt samples for examples 3–6. The feed salt samples heated to induce disproportionation were first prepared as mixed salts by stripping from aqueous solution, dried at 125° C. in a vacuum oven, then mixed with 5% by weight of dried ZnO powder, and ground with the ZnO in a micromill to produce a fine (5–10 micron) powder. The powder was then dried at 175° C. in a vacuum oven at 1–2 torr pressure. The dry powder at 175° C. was conveyed quickly through the atmosphere and charged into a 100 cc autoclave heated to 130° C. to ensure dryness, sealed, and purged repeatedly with $CO_2$ to remove most of the air and provide the gas cap for the disproportionation reaction. The autoclave was then fitted onto a "rotisserie" rack in a Blue M convection furnace designed to maintain temperature at about +/-2° C. and heated for the required time. Heat up and cool down in this oven require about 15 and 20 minutes respectively.

The oven is purged with nitrogen in the event a leak releases potentially flammable naphthalene over the heater in the air circulation pathway.

EXAMPLE 2—COMPARATIVE

Example 2 demonstrates the preparation of potassium naphthoate salts for use in disproportionation as typically prepared without excess base and teachings of the instant invention. In the comparative example, 5.0 g of mixed salts containing 0.99 to 1.00:1 K:2-NA ratio are prepared as described with 0.25 g of ZnO, charged into the autoclaves as described and heated at 450° C. for 1.5 hours. The resulting NDA/N ratio of the product is between 1.00 and 0.95 depending on the exact preparation (amount of carbonate, bicarbonate, crystal size, DSC trace, XRD pattern of product salt, uniformity of mixing, etc.). Conversion of 2-NA to products is from 80% to 99% depending on $CO_2$ pressure and exact conditions as described above. Selectivity to 2,6 NDA in the NDA product is more than 70%.

EXAMPLE 3

In Example 3, a ratio of inorganic (carbonate, bicarbonate) basic salts to 2-naphthoic acid of 1.3:1 is used to prepare 5.0 g of mixed salts. The resulting salt is prepared as described with 0.25 g of ZnO, and added as described to the autoclaves and heated for 1.5 hours with a 20 minute hold period at 420° C. and 70 minutes at 450° C. (including transient heating to the higher temperature). The resulting NDA to N ratio is an average of 1.15 in this case, indicating a surplus of up to ca. 20% of NDA. In this example, an average conversion of 2-NA salt of 94% is observed, with an average selectivity to 2,6 NDA of 88% of the total NDAs formed. As usual, the major other NDA salt formed is the 2,3 isomer.

EXAMPLE 4

In Example 4, the mixture of example 3 is heated to 450° C. directly. An NDA/N ratio of 1.03 to 1.14 is observed, indicating that carboxylation of the naphthoic acid may occur during the temperatures of conventional Henkel isomerization and the normal heat-up period, provided sufficient excess base is present.

EXAMPLE 5

In Example 5, a variety of K:2-NA ratios is used, from 1.2:1 to 2.0:1, with the slow heat up cycle of Example 3. The resulting NDA yields based on 2-NA conversion range up to 40% excess of theoretical yield from the disproportionation reaction. 2,3 NDA is the major non-2,6 NDA isomer formed, but again 2,6 NDA is typically about 80–90% of the total NDAs. An optimum appears around 1.3 to 1.6 to 1 K:2-NA ratio, probably due to an optimal level of mixing in the combined organic/inorganic (naphthoate/carbonate & bicarbonate) salts and dispersion of the catalyst. Additionally, it is thought that ratios of 2.0 to 1 or less are preferred strictly on yield grounds due the reduced level of naphthoate per unit volume in the high ratio materials. In addition, it is more difficult to recycle the salts at high ratios, due to reduced effectiveness of the preferred $CO_2$ precipitation of 2,6 NDA at high base levels. Therefore it is apparent that for a given process configuration, there will be an optimum level of excess base, an optimum temperature profile and residence time, etc.

EXAMPLE 6

In Example 6, the experiment of Example 3 is repeated with substitution of 9% of the potassium with Cs. It is observed that the NDA to N ratio is about 1.1:1. However, if the temperature is lowered to 430° C. it is also observed that the kinetics are substantially faster, with a greater rate of production of NDAs at 430° C. than at 450° C. in the pure potassium case. It is thought that the Cs/K mixture favors the disordered salt phase preferred for the carboxylation and disproportionation and isomerization reactions. It is further observed that eutectic mixtures of 1- and 2-napthoic acids as a mixed salt of Cs, K, and Rb may be formed over a fairly wide ratio of alkali ions and organic isomers. Such eutectics may melt as low as about 300° C., and give a rapid disproportionation and isomerization as well as carboxylation as low as 380° C. However, they are not generally the most preferred embodiment, due to the cost of the heavier alkali ions and the difficulties of separation in the $CO_2$ precipitation phase (oiling out of salts etc.).

EXAMPLE 7

Example 7 demonstrates a preferred embodiment of the present invention.

Two uniform master batches of potassium 2-naphthoate were prepared from 2-napthoic acid (2-NA), potassium bicarbonate (KHCO3), and powdered zinc oxide (ZnO), batch number 1 having a ratio of K:2-NA of 0.98–1, and batch 2 having a ratio of 1.17–1.19 K:2-NA. Batch 1 was prepared from 28.53 g of commercial KHCO3, 50.84 g of 2-NA, and 12.02 g of ZnO. The salt was prepared by boiling a solution of the $KHCO_3$ in excess water, with stirring and staged addition of the 2-NA and ZnO. The product salt and catalyst (ZnO) mixture was then collected and dried in a rotary evaporator and a vacuum oven at 175° C., for a total dry weight of 98% of theoretical. (The uncertainty in K:2-NA ratio is analytical uncertainty.) Batch 2 was prepared similarly from 34 g of KHCO3, 49.71 g of 2-NA, and 12.71 g of ZnO. Recovery of mixed salt and catalyst product after drying was in excess of 96% of theoretical weight. Batch 1 had 16.30% by weight of ZnO catalyst, Batch 2 had 16.5% weight of ZnO, a difference previously shown to be completely insignificant in terms of rates or yields. Samples of both batches were then separately ground in a mill to fine (ca. 5–10 micron) size, dried to 175° C. under 0.2 mm of mercury vacuum, and charged into a set of rotating autoclaves heated by a forced air convection furnace with temperature control to +/−2 degrees Centigrade or better. Three 100 cc autoclaves were charged with each mixture, 10 g per autoclave, and the autoclaves pressured to ca. 400 psig with $CO_2$ and then vented to atmospheric pressure three times each to remove any remaining air before a final pressuring to 400 psig and venting to 200 psig. The reaction was conducted under a gas cap of 200 psig of $CO_2$. The furnace was then activated, with the six autoclaves rotating, and heated to 450° C. over a period of about 15 minutes. The autoclaves were kept at 450° C. in the air bath for 1.5 hours of rotation, and cooled to ambient over about 20 minutes. The pressure was then released on each autoclave, and the content of the various NDA and NA salts determined by quantitative nuclear magnetic resonance (NMR) analysis in $D_2O$. The napthalene and other water insoluble hydrocarbon content of each sample was determined by digesting in d6 DMSO (deuterio dimethyl sulfoxide) with trioxane as the internal protonic standard. The nmr samples were digested for a period of 1–4 hours at elevated temperature depending on the analysis being performed. Each analysis was performed identically for each sample. Appropriate proton containing internal standards were used for each analysis to aid quantitation. The nmr quantitation had previously been demonstrated to be within 1% of the true amount of most of the NDA isomer salts. The results of 2,6 NDA production were as follows:

Batch 1: 27.43+/−5.73% of K2-2,6-NDA in the product
Batch 2: 48.39+/−4.26% of K2-2,6-NDA in the product.

These differences are highly significant, and prove that the use of excess base in the form of potassium bicarbonate in the mixture charged to the reactor greatly increases the yield of the desired 2,6 NDA. When compared against a theoretical result of 100% conversion of the K-2-NA salt to K2-2, 6-NDA salt, the results observed for Batch 1 indicate a yield of 47% (+/−9.8%) of theory and for Batch 2 indicate a yield of 89% of theory (+/−7.8%). This difference is due to a lesser conversion of 2,3 NDA to 2,6 NDA in the lower base (normal) case vs. the higher base (inventive) case, as well as significantly higher losses to naphthalene by decarboxylation (ca. 15% in the "normal" case vs. ca. 2% in the inventive case). (That is, the amount of napthalene made is >=1.15×theoretical in the "normal", Batch 1, case, and about 1.02×theoretical in the inventive case). Additionally, in the Batch1 product, significantly less 2-NA is converted into any sort of NDA. Thus the inventive process is clearly superior in terms of rate of production of the desired 2,6 product, total yield of said product with recycle of the other acids and diacids for further isomerization, reduced loss to naphthalene by decarboxylation, and concentration of K2-2,6-NDA in the product solids, leading to much simpler purification and recycle in the inventive high yield process.

The numbers above are given in terms of mean +/− standard deviation in each case. It can be seen that a further advantage of the inventive high yield process is that the variability of the process is reduced. Thus, for batch 1, the standard deviation was 21% of the mean, while for the inventive process, it was 8.8% of the mean. Therefore much less process variation is to be expected in the inventive process. In fact, kinetic studies have shown that after 1 hour at 450° C., the material of Batch 1 or related 1:1 K:2-NA ratio preparations may range from essentially unconverted to 2,6 NDA to results similar to those shown here, while the inventive high base compositions are much more uniformly related to the results observed here (e.g., typically 70% of the theoretical conversion to 2,6 NDA, with a similar variability to that observed in the examples above). Therefore variation in residence time, which could result in very low conversions for the "normal" 1:1 feed, only result in marginally diminished yields for the inventive high base (1.1 or greater: 1 K:NA) feed. This feature allows much smoother operation of the inventive process.

EXAMPLE 8

Example 8 was an experiment designed to show TGA reaction temperature onset as a function of overbasing. The overbasing ratio is the ratio of potassium in the base used to 2-naphthoic acid used to generate the salt. All mixtures contain ca. 17% ZnO.

The onset temperature of reaction by thermogravimetric analysis (TGA) is the temperature at which non-drying weight loss begins for the given system being heated at 10° C./min. under $N_2$ in this example. It is a measure of reactivity of the system, influenced by molecular mobility and carbonate: acid ratio. Naphthalene evolution has been demonstrated for these systems in a pyroprobe connected to a mass spectrometer, although it is possible in some instances the weight loss could begin with water from bicarbonate formed from the carboxylation reaction as discussed above. The low temperature peak is about 1/10 the size of the high temperature onset peak (typically 1.5–4% vs 20–30% weight loss). The low temperature peak would represent water (from carboxylation, drying occurring at much lower temperature) and the high temperature peak represents naphthalene of disproportionation in the simplest model. Some examples also exhibit an intermediate peak.

In this model, the lower temperature is then taken as the minimum temperature for the carboxylation reaction, and the upper temperature as the upper limit for carboxylation and lower limit for disproportionation. It is desirable to operate as near to the upper limit for carboxylation (higher temp.) as possible to achieve the maximum rate of carboxylation, but preferably below it, to avoid consumption of naphthoic acid by disproportionation before it can be carboxylated.

$KHCO_3$ is mostly converted to $K_2CO_3$ during the 175° C. drying (>75%) and is essentially completely converted by 300° C. Results are shown in Table 2:

TABLE 1

| Overbasing Ratio (a) | Base Used | Onset of reaction ° C. Low Temp Peak | Onset of reaction ° C. High Temp Peak |
|---|---|---|---|
| 1.0 | $K_2CO_3$ | 380 | 444 |
| 1.2 | $KHCO_3$ | 365 | 414 |
| 1.2 | $K_2CO_3$ | 250 | 420 |
| 1.4 | $K_2CO_3$ | 240 | 425 |
| 2.0 | $K_2CO_3$ | 280 | 420 |

We claim:

1. A process for disproportionation of an aromatic carboxylic acid to the corresponding salt and its isomers which comprises:
    a) Preparing a disproportionation feed comprising a solid salt mixture of excess base and aromatic acid by the steps of:
        1) Reacting said aromatic acid in the presence of excess base selected from the group consisting of carbonates and bicarbonates to form a salt mixture;
        2) Drying said salt mixture to form a solid salt mixture; and
    b) Disproportionating said solid salt mixture in the presence of a disproportionation catalyst.

2. The process of claim 1 wherein the aromatic carboxylic acid is naphthoic acid which is disproportionated to 2,6-naphthalene dicarboxylic acid and its isomers.

3. The process of claim 2 further comprising mixing the disproportionation catalyst with the excess base and naphthoic acid to form the salt mixture.

4. The process of claim 2 wherein the excess base is selected from the group consisting of alkali metal carbonates and alkali metal bicarbonates.

5. The process of claim 4 wherein the excess base is selected from the group consisting of $K_2CO_3$, $KHCO_3$, $Rb_2CO_3$, $RbHCO_3$, $Cs_2O_3$, and $CsHCO_3$.

6. The process of claim 1 wherein the base is selected from $K_2CO_3$ and $KHCO_3$.

7. The process of claim 2 wherein said napthoic acid is reacted in the presence of 0.001 to 0.30 moles of excess base.

8. The process of claim 6 wherein the ratio of potassium in the base to acid is in the range of 1.03–1.80 to 1, respectively.

9. The process of claim 8 wherein the ratio of potassium in the base to acid is in the range of 1.1–1.6 to 1, respectively.

10. The process of claim 9 wherein the ratio of potassium in the base to acid is in the range of 1.15–1.3 to 1.

11. The process of claim 2 wherein said salt mixture is characterized by one or more of the following "two theta" peaks in the powder X-ray diffraction patterns:
    14.0, 28.5, 38.2, 13.6, 27.3, 32.0, and 36.7 degrees two theta, corresponding to lattice spacings of 6.32, 3.13, 2.35, 6.52, 3.26, 2.80, and 2.45 Angstroms in Bragg d-spacing.

12. The process of claim 1 wherein said solid salt mixture is dried at a temperature of about 100–200° C. for 1–3 hours under 0.5–2 mm torr Hg pressure.

13. The process of claim 1 which further comprises drying said salt mixture by dripping the salt mixture into hot oil.

14. The process of claim 13 wherein the hot oil is naphthalene.

15. The process of claim 1 which further comprises drying said salt mixture by a method which quickly flashes water.

16. The process of claim 1 which further comprises drying said salt mixture by a method selected from spray drying and drying in a rotary evaporator or tumbler.

17. The process of claim 1 wherein said solid salt mixture contains less than 1000 ppm water.

18. The process of claim 1 wherein said solid salt mixture is intimately mixed.

19. The process of claim 1 wherein said solid salt mixture is characterized by a differential scanning calorimeter (DSC) signature characterized by low melting peaks not previously observed in the salt for the base or the acid.

20. The process of claim 1 wherein the disproportionation catalyst is selected from zinc compounds.

21. The process of claim 20 wherein the disproportionation catalyst is selected from zinc oxide and zinc naphthoate.

22. The process of claim 21 which further comprises disproportionating said solid salt mixture in the presence of a zinc oxide catalyst at a temperature in the range of less than 500° C. and less than 500 psig $CO_2$ to form the dipotassium salt of 2,6-naphthalene dicarboxylic acid and its isomers.

23. The process of claim 22 wherein the temperature is 420–460° C. and the pressure is greater than 100 psig.

24. The process of claim 23 wherein the pressure is about 225–275 psig.

25. A process for disproportionation of potassium naphthoate to the dipotassium salt of 2,6-naphthalene dicarboxylic acid and its isomers which provides reproducible improved yields comprising the steps of:
    a) Reacting naphthoic acid in the presence of excess base selected from the group consisting of carbonates and bicarbonates to form a salt mixture;
    b) Drying said salt mixture to form a solid salt mixture; and
    c) Disproportionating said solid salt mixture in the presence of a disproportionation catalyst to form the dipotassium salts of 2,6-naphthalene dicarboxylic acid and its isomers.

26. The process of claim 2 wherein the excess base is selected from the group consisting of alkali metal bicarbonates.

27. The process of claim 26 wherein the excess base is selected from the group consisting of $KHCO_3$, $RbHCO_3$, and $CsHCO_3$.

28. The process of claim 27 wherein the excess base is $KHCO_3$.

* * * * *